United States Statutory Invention Registration [19]

[11] Reg. Number: H328

Koizumi et al. [43] Published: Sep. 1, 1987

[54] PURIFICATION OF CEPHALOSPORINS

[75] Inventors: Hiroaki Koizumi; Satoru Kawatake; Kanji Tokuyama, all of Osaka, Japan

[73] Assignee: Shionogi & Co., Ltd., Osaka, Japan

[21] Appl. No.: 696,430

[22] Filed: Jan. 30, 1985

[30] Foreign Application Priority Data

Feb. 2, 1984 [JP] Japan ..... 59-17699

[51] Int. Cl.[4] ..... C07D 265/12

[52] U.S. Cl. ..... 544/90

*Primary Examiner*—Deborah L. Kyle
*Assistant Examiner*—T. J. Wallen
*Attorney, Agent, or Firm*—Wenderoth, Lind & Ponack

[57] ABSTRACT

A process for purifying oxacephalosporins which comprises contacting an aqueous solution of oxacephalosporin carboxylic acid (at pH lower than its pKa) with a macroporous polymeric adsorbent (specific gravity: higher than 1.05; and saturated adsorption capacity for cephalosporin C. larger than 60 mg/ml) to adsorb and thereby separate the oxacephalosporin carboxylic acid from non-adsorbable contaminants, and then eluting the adsorbed oxacephalosporin carboxylic acid with an aqueous hydrophilic organic solvent to elute and thereby separate it from non-eluting contaminants.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PURIFICATION OF CEPHALOSPORINS

This invention relates to a process for purifying oxacephalosporins useful as antibacterials. More specifically, it relates to a process for purifying oxacephalosporin carboxylic acids which comprises contacting an aqueous solution of the oxacephalosporin carboxylic acid (at pH lower than its pKa) with a macroporous polymeric adsorbent (specific gravity: higher than 1.05; and saturated adsorption capacity for cephalosporin C: larger than 60 mg/ml, i.e., more than 1.2 times as high as adsorbents reported in the literature to separate non-adsorbable contaminants therefrom, and then eluting it with an aqueous hydrophilic organic solvent to separate from non-eluting contaminants therefrom.

In the production of oxacephalosporins, contaminants are removed by repeated extraction, precipitation, crystallization, adsorption by old type synthetic adsorbents (e.g., Amberlite XAD-2, XAD-4, XAD-7, XAD-8, Diaion HP-10, HP-20, HP-30, HP-40, and HP-50), elution, or the like in the work up.

The present inventors looked for a suitable method to promote efficiency of the purification and completed this invention for purifying it with a macroporous polymeric adsorbent (specific gravity: higher than 1.05; and saturated adsorption capacity for cephalosporin C: larger than 60 mg/ml, i.e., more than 1.2 times as high as adsorbent written in the citations).

It is known to use macroporous polymeric adsorbents to remove electro-neutral materials, low molecular weight substances, or the like from cephalosporin aqueous solutions [e.g., Japanese Patent Publication (Kokoku) SHO-52-50799, 54-16922; and Japanese Patent Application Publication (Kokai) SHO-50-106996, 51-110587, etc.]. However, the known methods have several defects (e.g., lower adsorption capacity of the resins, turbidity of eluted solvent, and difficulty of handling due to low specific gravity).

In contrast, the macroporous polymeric adsorbent of this invention (having specific gravity of higher than 1.05 and saturated adsorption capacity for cephalosporin C of larger than 60 mg/ml., i.e., more than 1.2 times as high as adsorbents written in the literatures) has no such defect, and it is suitable for purifying the unstable oxacephalosporin free carboxylic acids.

Typical nonionic macroporus polymeric adsorbents are Amberlite XAD-2000, a stylene divinylbenzene copolymer resin produced by Rohm and Haas Co., and Diaion SP-206 and SP-207, styrene divinylbenzene copolymer resins produced by Mitsubishi Chemical Industries Limited.

The oxacephalosporin to be purified by this invention is 1-dethia-1-oxa-3-cephem-4-carboxylic acid or its derivative having at least one carboxy and having acylamino at position 7$\beta$, hydrogen or methoxy at position 7$\alpha$, and R or $CH_2R$ group at position 3 (here, R is hydrogen, halogen, alkyl, carbamoyl, carboxy, hydroxy, alkoxy, acyloxy, alkylthio, haloalkylthio, arylthio, heterocyclic thio, pyridinium, substituted pyridinium, or the like nucleophilic group). The acyl in the acylamino is that of the amido side chain in the penicillin or cephalosporin chemistry. The heterocyclic group is mono- or di-cyclic heterocyclic group having one or more hetero atom selected from nitrogen, oxygen, and sulfur and optionally substituted by alkyl or R-substituted alkyl. The said parts may have R or other conventional substituent in the cephalosporin moiety.

The amount of the macroporous polymeric resin used in this invention (having specific gravity of higher than 1.05 and saturated adsorption capacity for cephalosporin C of larger than 60 mg/ml, i.e., more than 1.2 times as high as adsorbents written in the literatures) is preferably 5 to 100 times the weight of the feeding oxacephalosporin free carboxylic acid.

The concentration of the oxacephalosporin carboxylic acid is preferably 0.1 to 30 w/w %. Preferably, the solution contains no adsorption inhibiting substance (for example, an organic solvent) over the inihibiting concentration. The operating temperature is preferably 0° to 50° C.

Adsorption is effected by contacting the aqueous solution of oxacephalosporin with the said macroporous polymer adsorbent by a conventional method (e.g., batch method, column method, or chromatographic method).

In order to remove non-adsorbable materials from the adsorbed material, the resin on which oxacephalosporin has been adsorbed is washed with a liquid which can wash out the non-adsorbable contaminants without eluting the desired substance. Such liquid can be, for example, water, buffer solution, salt solution, aqueous surfactant solution, or the like. Here again, a conventional method (e.g., batch method, column method, chromatographic method, or gradient method) is applicable. The washing can be continued until no impurity detectable in the effluents from the resin. The preferable temperature is 0° to 50° C.

For eluting the adsorbed objective material, it is preferable to use an aqueous organic solvent (e.g., ester, ketone, alcohol, or ether, especially lower alkanol). This may contain a substance for controlling eluting efficiency or independent of eluting (e.g., inorganic salt, acid, base, or cation surfactant). This elution may be carried out in a conventional operation (e.g., batch method, column method, chromatographic method, or gradient method), preferably at 0° to 50° C. The eluting procedure is stopped when the objective material has been eluted and the non-eluting contaminants remain on the adsorbent.

The used adsorbent can be recovered for using again in a usual operation (with, e.g., aqueous sodium hydroxide, neutral or acidic methanol or isopropanol, or mixture of these).

The oxacephalosporin can be recovered from the effluents by a conventional operation (e.g., extraction, concentration, precipitation, crystallization, of lyophilization).

Each step of this invention can be carried out at room temperature or at 0° to 50° C. for 30 minutes to 50 hours.

The oxacephalosporin carboxylic acids produced by this invention with low energy consumption is highly pure and highly yielding.

The following examples illustrate embodiments of this invention.

EXAMPLE 1.

A 0.11% crude latamoxef sodium [i.e., 7$\beta$-(2-p-hydroxyphenyl-2-carboxyacetamido)-3-(1-methyltetrazol-5-yl]thiomethyl-7$\alpha$-methoxy-1-dethia-1-dethia-1-oxa-3-cephem-4-carboxylic acid disodium salt] aqueous solution (produced by hydrolyzing latamoxef dibenzhydryl ester with aluminum chloride and by removing organic solvents from the reaction mixture) is adjusted pH to 1.5 with hydrochloric acid.

A nonionic macroporous polymeric adsorbent (Amberlite XAD-2000, a stylene-divinylbenzene copolymer adsorbent resin produced by Rohm and Haas Co.) (200 ml) is packed in 270 mm height in a glass tube which has 32 mm inside diameter and 350 mm length. The said solution (2780 g) is passed through the packed column to adsorb latamoxef. This column is washed with water (1360 ml) and then with 50% methanol (125 ml) to remove non-adsorbing contaminants (e.g., salts). Then, latamoxef is eluted with 70% methanol (535 ml). The effluents contain the objective material at a concentration of 0.5% when estimated ultraviolet spectrophotometerically.

The effluents are concentrated under diminished pressure, neutralized with aqueous sodium hydroxide, and lyophilized to obtain pure latamoxef sodium. Yield: 86%.

EXAMPLE 2.

A 0.19% crude latamoxef aqueous solution is adjusted pH to 2.9.

A nonionic macroporous polymeric adsorbent (Amberlite XAD-2000, a stylene-divinylbenzene copolymer resin produced by Rohm and Haas Co.) (100 ml) is packed in 255 mm height in a glass tube which has 22 mm inside diameter. The said solution (4800 ml; containing 8.02 g of the said compound) is passed through the packed column to adsorb the objective material. This column is washed with water (2480 ml). Then purified objective material is eluted with 50 to 80% methanol (810 ml). The effluents contain 68.7% of the feeding objective material when estimated ultra-violet spectrophotometrically.

EXAMPLE 3.

A 0.94% crude latamoxef aqueous solution is adjusted pH to 2 to 3.

A nonionic macroporous polymeric adsorbent (Diaion SP-207, a stylene-divinylbenzene copolymer resin produced by Mitsubishi Chemical Industries Limited) (40 ml) is packed in 115 mm height in a glass tube which has 19 mm inside diameter. The said solution (200 ml; containing 1.88 g of the said compound) is passed through the packed column to adsorb latamoxef. This column is washed with water (200 ml). Then the purified objective material is eluted with 50% acetone (220 ml). The effluents contain 93.3% of the feed objective material when estimated from high precision liquid chromatogram.

Similarly, the eluting solvent, 50% acetone, can be replaced by 70% isopropanol to obtain the same pure product in high yield.

EXAMPLE 4

A 1.0% crude 7β-difluoromethylthioacetamido-3-[1-(2-hydroxyethyl)tetrazol-5-yl]thiomethyl-7α-methoxy-1-dethia-1-oxa-3-cephem-4-carboxylic acid aqueous solution is adjusted pH to about 2.

A nonionic macroporous polymeric adsorbent (Diaion SP-207, a stylene-divinylbenzene copolymer adsorbent resin produced by Mitsubishi Chemical Industries Limited) (40 ml) is packed in 105 mm height in a glass tube which has 22 mm inside diameter. The solution (210 ml; containing 2.0 g of the said compound) is passed through the packed column to adsorb the objective material. This column is washed with water (100 ml). Then purified objective material is eluted with 70% isopropanol (140 ml). The effluents contain 87.1% of the feeding objective material when estimated ultra-violet spectrophotometrically.

EXAMPLE 5

A 1.0% crude 7β-difluoromethylthioacetamido-3-[1-(2-hydroxyethyl)tetrazol-5-yl]thiomethyl-7α-methoxy-1-dethia-1-oxa-3-cephem-4-carboxylic acid aqueous solution is adjusted pH to about 2.

A nonionic macroporous polymeric adsorbent (Amberlite XAD-2000, a stylene-divinylbenzene copolymer adsorbent resin produced by Rohm and Haas Co.) (30 ml) is packed in 275 mm height in a glass tube which has 12 mm inside diameter. The said solution (200 Ml; containing 2.0 g or the said compound) is passed through the packed column to adsorb the objective material. This column is washed with water (300 ml). Then purified objective material is eluted with 70% isopropanol (80 ml). The effluents contain 99.4% of the feed objective material when estimated ultra-violet spectrophotometrically.

EXAMPLE 6

A 0.15% crude 7β-[2-2-carbamoyl-2-fluorovinylthio)acetamido]-3-[1-(2-hydroxyethyl)tetrazol-5-yl]thiomethyl-7α-methoxy-1-dethia-1-oxa-3-cephem-4-carboxylic acid aqueous solution is adjusted pH to about 2.

A nonionic macroporous polymeric adsorbent (Diaion SP-207, a stylene-divinylbenzene copolymer resin produced by Mitsubishi Chemical Industries Limited) (30 ml) is packed in 132 mm height in a glass tube which has 16 mm inside diameter. The said solution (200 ml; containing 0.3 g of the said compound) is passed through the packed column to adsorb the objective material. This column is washed with water (200 ml). Then the purified objective material is eluted with 70% isopropanol (150 ml). The effluents contain 77.5% of the feeding objective material when estimated ultra-violet spectrophotometrically.

What we claim is:

1. A process for purifying oxacephalosporins which comprises contacting an aqueous solution of oxacephalosporin carboxylic acid (at pH lower than its pKa) with a macroporous polymeric adsorbent (specific gravity is higher than 1.05; and saturated adsorption capacity for cephalosporin C is larger than 60 mg/ml) to adsorb and thereby separate the oxacephalsporin carboxylic acid from non-adsorbable contaminants, and then eluting the adsorbed oxacephalosporin carboxylic acid with an aqueous hydrophilic organic solvent to elute and thereby separate the oxacephalosporin carboxylic acid from non-eluting contaminants.

2. The process as claimed in claim 1 wherein the process is carried out at 0° to 50° C.

3. The process as claimed in claim 1 wherein the oxacephalosporin carboxylic acid is latamoxef, 7β-difluoromethylthioacetamido-3-[1-(2-hydroxyethyl)tetrazol-5-yl]thiomethyl-7α-methoxy-1-dethia-1-oxa-3-cephem-4-carboxylic acid, or 7β-[2-(2-carbamoyl-2-fluorovinylthio)acetamido]-3-[1-(2-hydroxyethyl)tetrazol-5-yl]thiomethyl-7α-methoxy-1-dethia-1-oxa-3-cephem-4-carboxylic acid.

4. The process as claimed in claim 1 wherein the macroporous polymeric adsorbent is Amberlite XAD-2000, Diaion SP-206, or Diaion SP-207.

5. The process as claimed in claim 1 wherein amount of the macroporous polymeric adsorbent is 5 to 100 times the weight of the aqueous solution of oxacephalosporin carboxylic acid.

6. The process as claimed in claim 1 wherein the eluting solvent is 50 to 80% methanol, ethanol, propanol, isopropanol, or acetone aqueous solution.

* * * * *